(12) United States Patent
Wu et al.

(10) Patent No.: US 11,557,391 B2
(45) Date of Patent: Jan. 17, 2023

(54) SYSTEMS AND METHODS FOR HUMAN POSE AND SHAPE RECOVERY

(71) Applicant: SHANGHAI UNITED IMAGING INTELLIGENCE CO., LTD., Shanghai (CN)

(72) Inventors: Ziyan Wu, Lexington, MA (US); Srikrishna Karanam, Brighton, MA (US); Changjiang Cai, Secaucus, NJ (US); Georgios Georgakis, Philadelphia, PA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 262 days.

(21) Appl. No.: 16/995,446

(22) Filed: Aug. 17, 2020

(65) Prior Publication Data
US 2021/0158028 A1 May 27, 2021

Related U.S. Application Data

(60) Provisional application No. 62/941,203, filed on Nov. 27, 2019.

(51) Int. Cl.
*G06K 9/62* (2022.01)
*G16H 30/40* (2018.01)
(Continued)

(52) U.S. Cl.
CPC ........... *G16H 30/40* (2018.01); *A61B 5/0035* (2013.01); *A61B 5/70* (2013.01); *G06K 9/6217* (2013.01);
(Continued)

(58) Field of Classification Search
None
See application file for complete search history.

(56) References Cited

U.S. PATENT DOCUMENTS

| 6,057,859 A | * | 5/2000 | Handelman | G06T 13/40 |
| | | | | 345/475 |
| 6,552,729 B1 | * | 4/2003 | Di Bernardo | G06T 13/20 |
| | | | | 345/473 |

(Continued)

OTHER PUBLICATIONS

"Hoang et al., An Improved Method for 3D Shape Estimation Using Cascade of Neural Networks" (Year: 2017).*
(Continued)

*Primary Examiner* — Hilina K Demeter
(74) *Attorney, Agent, or Firm* — Zhong Law, LLC

(57) ABSTRACT

The pose and shape of a human body may be recovered based on joint location information associated with the human body. The joint location information may be derived based on an image of the human body or from an output of a human motion capture system. The recovery of the pose and shape of the human body may be performed by a computer-implemented artificial neural network (ANN) trained to perform the recovery task using training datasets that include paired joint location information and human model parameters. The training of the ANN may be conducted in accordance with multiple constraints designed to improve the accuracy of the recovery and by artificially manipulating the training data so that the ANN can learn to recover the pose and shape of the human body even with partially observed joint locations.

16 Claims, 4 Drawing Sheets

(51) Int. Cl.

| | | |
|---|---|---|
| G06T 7/00 | (2017.01) | |
| G06T 7/90 | (2017.01) | |
| G06T 17/00 | (2006.01) | |
| G06T 7/50 | (2017.01) | |
| G06T 7/70 | (2017.01) | |
| G06T 17/20 | (2006.01) | |
| G16H 10/60 | (2018.01) | |
| G16H 30/20 | (2018.01) | |
| A61B 5/00 | (2006.01) | |
| G06V 10/40 | (2022.01) | |
| G06V 10/42 | (2022.01) | |
| G06V 20/64 | (2022.01) | |
| G06V 40/10 | (2022.01) | |
| G06V 40/20 | (2022.01) | |
| G06V 20/62 | (2022.01) | |

(52) U.S. Cl.
CPC ......... *G06K 9/6256* (2013.01); *G06K 9/6265* (2013.01); *G06T 7/0012* (2013.01); *G06T 7/50* (2017.01); *G06T 7/70* (2017.01); *G06T 7/90* (2017.01); *G06T 17/00* (2013.01); *G06T 17/20* (2013.01); *G06V 10/40* (2022.01); *G06V 10/42* (2022.01); *G06V 20/62* (2022.01); *G06V 20/64* (2022.01); *G06V 40/10* (2022.01); *G06V 40/20* (2022.01); *G16H 10/60* (2018.01); *G16H 30/20* (2018.01); *G06T 2200/08* (2013.01); *G06T 2207/10024* (2013.01); *G06T 2207/20081* (2013.01); *G06T 2207/20084* (2013.01); *G06T 2207/30004* (2013.01); *G06T 2207/30196* (2013.01); *G06V 2201/033* (2022.01)

(56) References Cited

U.S. PATENT DOCUMENTS

| | | | | |
|---|---|---|---|---|
| 10,679,046 | B1* | 6/2020 | Black | G06N 3/0454 |
| 10,839,586 | B1* | 11/2020 | Nemchinov | G06T 3/0037 |
| 2012/0056800 | A1* | 3/2012 | Williams | G06V 40/103 |
| | | | | 345/156 |
| 2019/0116322 | A1* | 4/2019 | Holzer | G06V 10/34 |
| 2019/0130602 | A1* | 5/2019 | Hall | G06V 40/23 |
| 2019/0266780 | A1* | 8/2019 | Le | G06T 7/75 |
| 2019/0340803 | A1* | 11/2019 | Comer | G06T 13/40 |
| 2019/0371080 | A1* | 12/2019 | Sminchisescu | G06T 13/40 |
| 2020/0184721 | A1* | 6/2020 | Ge | G06N 3/08 |
| 2020/0193671 | A1* | 6/2020 | Tamir | G06T 7/251 |
| 2020/0410736 | A1* | 12/2020 | Lu | G06N 3/0454 |

OTHER PUBLICATIONS

"Madadi et al., Deep SMPL Reverse for 3D Human pose and shape Recovery" (Year: 2018).*
Wei et al., "Convolutional Pose Machines" CVF, 2016, pp. 4724-1732.
Zhou et al., "Towards 3D Human Pose Estimation in theWild: aWeakly-supervised Approach", CVF, 2017, pp. 398-407.
Zimmermann et al., "3D Human Pose Estimation in RGBD Images for Robotic Task Learning",arXiv:1803.02622v2 [cs.CV] Mar. 13, 2018, pp. 1-7.
Guler et al., "DensePose: Dense Human Pose Estimation in the Wild", 2018, CVF, pp. 7297-7306.
Arnab et al., "Exploting Temporal Context for 3D Human Pose Estimation in the Wild", 2019, CVF, pp. 3395-3404.
Bahdanau et al., "Neural Machine Translation by Jointly Learning to Align and Translate", ICLR, 2015, arXiv:1409.0473v7 [cs.CL], pp. 1-15.
Belghit et al., "Vision-Based Pose Estimation for Augmented Reality: A Comparison Study", IEEE, 2018, pp. 1-8.
Bogo et al., "Keep It SMPL: Automatic Estimation of 3D Human Pose and Shape from a Single Image", Computer Vision and Pattern Recognition, 2016, pp. 561-578.
Cao et al., "Realtime Multi-Person 2D Pose Estimation Using Part Affinity Fields", CVF, 2017, pp. 7291-7299.
Chen et al., 3D Human Pose Estimation + 2D Pose Estimation + Matching, CVF, 2016, pp. 7035-7043.
Chen et al., "Synthesizing Training Images for Boosting Human 3D Pose Estimation", arXiv:1604.02703v6 [cs.CV] Jan. 5, 2017, pp. 4321-4330.
Chen et al., "Weakly-Supervised Discovery of Geometry-Aware Representation for 3D Human Pose Estimation", CVF, 2019, pp. 10895-10904.
Liu et al., "PKU-MMD: A Large Scale Benchmark for Continuous Multi-Modal Human Action Understanding", arXiv:1703.07475v2 [cs.CV] Mar. 28, 2017, pp. 1-10.
Deprelle et al., "Learning Elementary Structures for 3D Shape Generation and Matching", arXiv:1908.04725v2 [cs.CV] Aug. 14, 2019, pp. 1-11.
Groueix et al., "3D-Coded: 3D Correspondences by Deep Deformation", CVF, 2018, pp. 1-17.
Gupta et al., "3D Pose from Motion for Cross-View Action Recognition via Non-linear Circulant Temporal Encoding", CVF, 2014, pp. 1-8.
He et al., "Deep Residual Learning for Image Recognition", CVF, 2015, pp. 770-778.
He et al., "Identity Mappings in Deep Residual Networks", arXiv:1603.05027v3 [cs.CV] Jul. 25, 2016. pp. 1-15.
Jahangiri et al., "Generating Multiple Diverse Hypotheses for Human 3D Pose Consistent with 2D Joint Detections", IEEE, 2017, pp. 805-814.
Hao Jiang, "3D Human Pose Reconstruction Using Millions of Exemplars", International Conference on Pattern Recognition, 2010, pp. 1674-1677.
Johnson et al., "Clustered Pose and Nonlinear Appearance Models for Human Pose Estimation", BMVC, 2010, pp. 1-11.
Kadkhodamohammadi et al., "A Multi-View RGB-D Approach for Human Pose Estimation in Operating Rooms, "IEEE, 2017, pp. 363-372.
Kanazawa et al., "End-To-End Recovery of Human Shape and Pose", CVF, 2017, pp. 7122-7131.
Kanazawa et al., "Learning 3D Human Dynamics from Video", CVF, 2019, pp. 5614-5623.
Kocabas et al., "Self-Supervised Learning of 3D Human Pose Using Multi-View Geometry", CVF, 2019, pp. 1077-1086.
Kohli et al., "Key Developments in Human Pose Estimation for Kinect", Advances in Computer Vision and Pattern Recognition, 2013, pp. 63-70.
Kolotouros et al., "Convolutional Mesh Regression for Single-Image Human Shape Reconstruction", CVF, 2019, pp. 4501-4510.
Lassner et al., "Unite the People: Closing the Loop Between 3D and 2D Human Representations", CVF, 2017, pp. 6050-6059.
Levine et al., "End-To-End Training of Deep Visuomotor Policies", Journal of Machine Learning Research 17, 2016, pp. 1-40.
Liang et al., "Shape-Aware Human Pose and Shape Reconstruction Using Multi-View Images", CVF, 2019, pp. 4352-4362.
Lin et al., "Microsoft COCO: Common Objects in Context", Springer International Publishing Switzerland, 2014, pp. 740-755.
Looper et al., "MoSh: Motion and Shape Capture from Sparse Markers", ACM Transactions on Graphics, vol. 33, No. 6, 2014, pp. 1-13.
Looper et al., "SMPL: A Skinned Multi-Person Linear Model", ACM Transactions on Graphics, 2015, pp. 1-16.
Martinez et al., "A Simple Yet Effective Baseline for 3D Human Pose Estimation", CVF, 2017, pp. 2640-2649.
Martinez-Gonzalez et al., "Reall-time Convolutional Networks for Depth-Based Human Pose Estimation", IDIAP Research Institute, 2018, pp. 1-7.
Mehta et al., "VNect: Real-time 3D Human Pose Estimation with a Single RGB Camera", ACM Transactions on Graphics, vol. 36, No. 4, 2017, pp. 1-14.

(56) References Cited

OTHER PUBLICATIONS

Moeslund et al., "A Survey of Computer Vision-Based Human Motion Capture" Computer Vision and Image Understanding 81, 2001, pp. 231-268.

Moeslund et al., "A Survey of Advances in Vision-Based Human Motion Capture", ELSEVIER, 2006, pp. 90-126.

Newell et al., "Stacked Hourglass Networks for Human Pose Estimation", arXiv:1603.06937v2 [cs.CV] Jul. 26, 2016, pp. 1-17.

Obdrzalek et al., "Accuracy and Robustness of Kinect Pose Estimation in the Context of Coaching of Elderly Population", IEEE, 2012, pp. 1188-1193.

Paszke et al., "Automatic Differentiation in PyTorch" 31st Conference on Neural Information Processing Systems, 2017, pp. 1-4.

Pavlakos et al., "Ordinal Depth Supervision for 3D Human Pose Estimation", CVF, 2018, pp. 7307-7316.

Pavlakos et al., "Coarse-To-Fine Volumetric Prediction for Single-Image 3D Human Pose", CVF, 2017, pp. 7025-7034.

Peng et al., "Jointly Optimize Data Augmentation and Network Training Adversarial Data Augmentation in Human Pose Estimation", CVF, 2018, pp. 2226-2234.

Rhodin et al., "Neural Scene Decomposition for Multi-Person Motion Capture", CVF, 2019, pp. 7703-7713.

Rhodin et al., "Unsupervised Geometry-Aware Representation for 3D Human Pose Estimation", CVF 2018, pp. 1-18.

Rogez et al., "MoCap-Guided Data Augmentation for 3D Pose Estimation in the Wild", Computer Vision and Pattern Recognition, 2016, pp. 1-9.

Sarafianos et al., "3D Human Pose Estimation: A Review of the Literature and Analysis of Covariates" Elsevier, Computer Vision and Image Understanding, 2016, pp. 1-20.

Sharma et al., "Monocular 3D Human Pose Estimation by Generation and Ordinal Ranking", CVF, 2019, pp. 2325-2334.

Sun et al., "Integral Human Pose Regression" CVF, 2018, pp. 1-17.

Sung et al., "Unstructured Human Activity Detection from RGBD Images", IEEE, 2012, pp. 1-8.

Varol et al., "Learning from Synthetic Humans", CVF, 2017, pp. 109-117.

Wandt et al., "RepNet: Weakly Supervised Training of an Adversarial Reprojection Network for 3D Human Pose Estimation", CVF, 2019, pp. 7782-7791.

\* cited by examiner

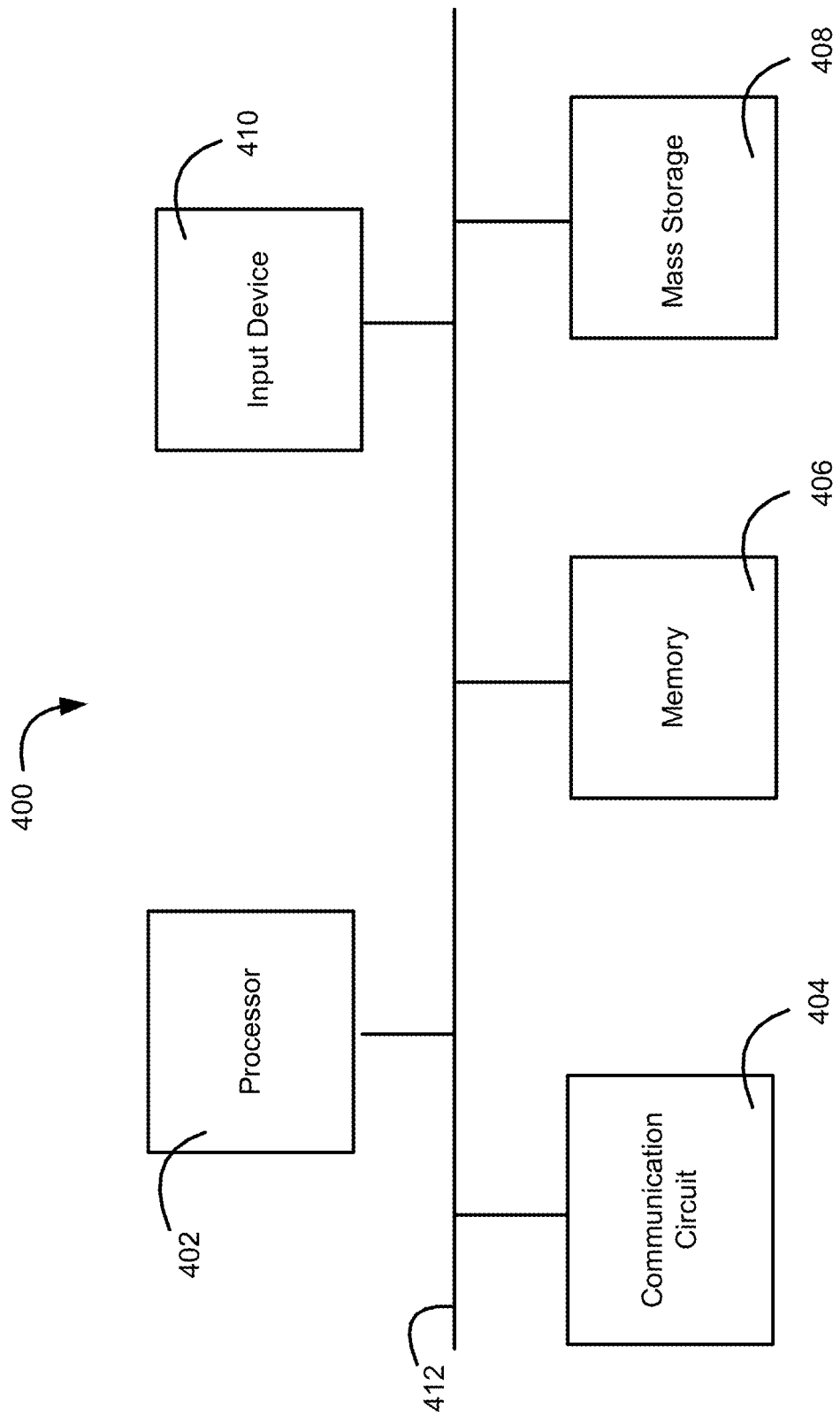

SYSTEMS AND METHODS FOR HUMAN POSE AND SHAPE RECOVERY

CROSS-REFERENCE TO RELATED APPLICATIONS

This application claims the benefit of Provisional U.S. Patent Application No. 62/941,203, filed Nov. 27, 2019, the disclosure of which is incorporated herein by reference in its entirety.

BACKGROUND

Computer-generated human body models that realistically represent a patient's pose and shape can be used in a wide range of medical applications including, e.g., patient positioning, surgical navigation, unified medical record analysis, etc. For instance, in radiation therapy and medical imaging, success often hinges on the ability to place and maintain a patient in a desirable position so that the treatment or scan can be performed in a precise and accurate manner. Having real time knowledge about the patient's physical characteristics such as the patient's body shape and pose in these situations may bring many benefits such as faster and more accurate positioning of the patient in accordance with a scan or treatment protocol, more consistent results across multiple scans or treatment sessions, etc. In other example situations such as during surgical procedure, information about a patient's physiques may offer insight and guidance for both surgery planning and execution. For instance, the information may be utilized to locate and navigate around a surgical area of the patient. And when visually presented in real time, the information may also provide means for monitoring the state of the patient during the procedure.

Conventional techniques for recovering a human model for a patient rely on having comprehensive knowledge about the joint locations of the patient and may only be able to recover the pose of the patient based on the joint location. In many medical settings, however, a patient's body is often blocked, at least partially, by medical equipment and/or clothing items, and it may also be beneficial in those settings to obtain information about the body shape of the patient. Therefore, it is highly desirable to have the ability to recover both the pose and shape of a patient despite only having limited information about the physical characteristics of the patient.

SUMMARY

Described herein are systems, methods and instrumentalities for recovering the pose and shape of a person based on one or more joint locations of the person. The joint locations may be determined based on an image of the person such as an image that includes color and/or depth information representing the physical characteristics of the person. The joint locations may be a subset of all joint locations of the person (e.g., not including joints that are obstructed or otherwise unknown). The systems, methods and instrumentalities may include one or more processors and one or more storage devices storing instructions that, when executed by the one or more processors, cause the one or more processors to implement an artificial neural network and provide information regarding the one or more joint locations of the person to the artificial neural network. The artificial neural network may determine a first plurality of parameters associated with a pose of the person and a second plurality of parameters associated with a shape of the person based on the information regarding the one or more joint locations of the person. Based on the first and second pluralities of parameters, one or more human models may be generated that represent the pose and shape of the person.

The artificial neural network may be trained to perform one or more of the tasks described above using training data that comprises joint locations of a human body. During the training, the artificial neural network may predict pose and shape parameters associated with the human body based on the joint locations comprised in the training data. The artificial neural network may then infer joint locations of the human body from the predicted pose and shape parameters, and adjust (e.g., optimize) the operating parameters (e.g., weights) of the artificial neural network based on a difference between the inferred joint locations and the joint locations comprised in the training data. In examples, the training data may also comprise pose and shape parameters associated with the joint locations of the human body and the artificial neural network may adjust (e.g., optimize) its operating parameters further based on a difference between the predicted pose and shape parameters and the pose and shape parameters comprised in the training data.

To acquire the ability to predict the pose and shape parameters based on partial knowledge about the joint locations of a person (e.g., certain joint locations of the person may be obstructed, unobserved or otherwise unknown to the neural network), the training of the artificial neural network may involve providing a subset of joint locations to the artificial neural network and forcing the artificial neural network to predict the pose and shape parameters using the subset of joint locations. For instance, the training may utilize an existing parametric human model associated with a human body to determine a plurality of joint locations of the human body and then randomly exclude a subset of the plurality of joint locations from the input of the artificial neural network (e.g., by artificially treating the subset of joint locations as unobserved and unavailable).

The joint locations described herein may include two-dimensional (2D) and/or three-dimensional (3D) joint locations of a person. When the training is conducted using at least 2D joint locations, the artificial neural network may, during the training, predict pose and shape parameters based on the 2D joint locations, infer 3D joint locations of the human body using the predicted pose and shape parameters, and project the 3D joint locations into an image space to obtain corresponding 2D joint locations. The artificial neural network may then adjust its operating parameters based on a difference between the projected 2D joint locations and the 2D joint locations comprised in the training data.

The pose and shape parameters described herein may be recovered separately (e.g., independent of each other). For example, the pose parameters recovered may be body shape independent (e.g., independent of the height and weight of the person). Hence, in addition to medical applications, the techniques described herein may be used with various human motion capture systems (e.g., which may output 3D joint locations), for example, in game development, animation development, special effects for motion pictures, etc.

BRIEF DESCRIPTION OF THE DRAWINGS

A more detailed understanding of the examples disclosed herein may be had from the following description, given by way of example in conjunction with the accompanying drawing.

FIG. 4 is a block diagram illustrating an example neural network system as described herein.

DETAILED DESCRIPTION

The present disclosure is illustrated by way of example, and not by way of limitation, in the figures of the accompanying drawings.

Figure 1:
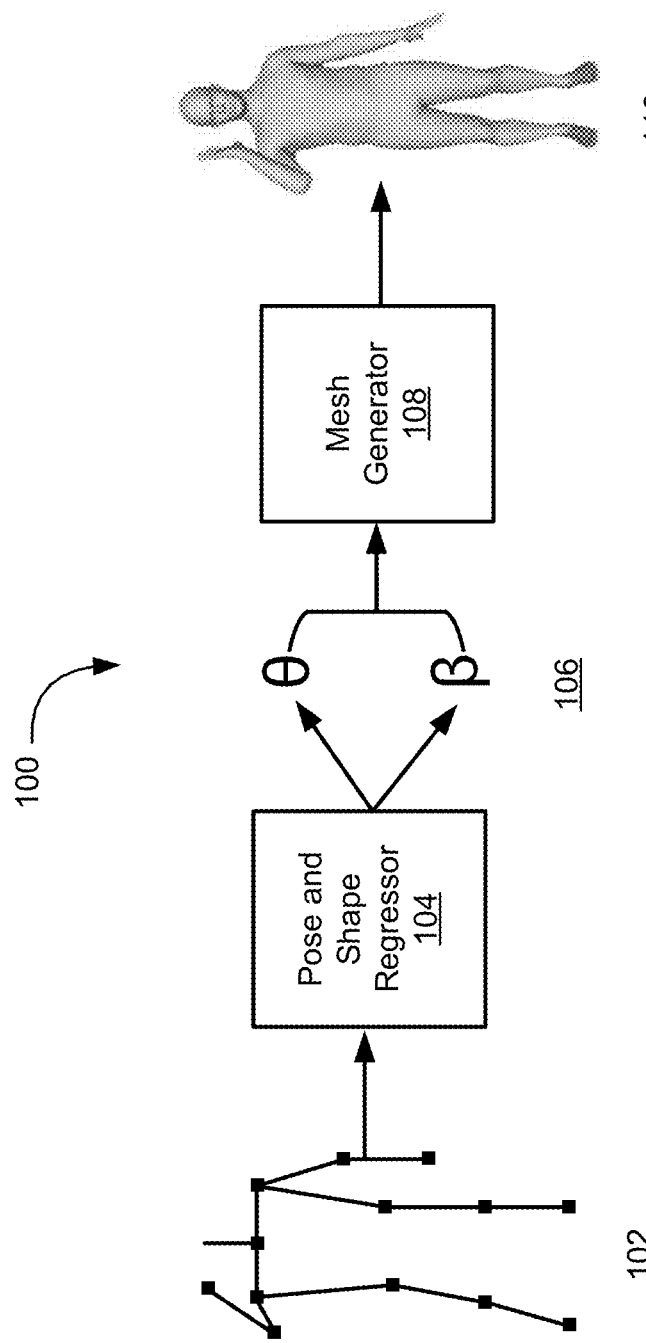
FIG. 1 is a block diagram illustrating an example system for recovering the pose and shape of a person based on joint location information associated with the person.

FIG. 1 is a diagram illustrating an example system 100 configured to recover the pose and shape of a person and generate a human model representing such recovered pose and shape of the person based on joint location information associated with the person. As shown, the system 100 may be configured to receive information regarding the joint locations 102 of a person. The joint locations 102 may include 2D joint locations (e.g., 2D coordinates, 2D keypoints, 2D feature maps (binary heatmaps), etc., that represent the 2D joint locations). The joint locations 102 may include 3D joint locations (e.g., 3D coordinates, 3D keypoints, 3D feature maps, etc., that represent the 3D joint locations). The joint locations 102 may also include a combination of 2D and 3D joint locations. The joint locations 102 may be derived from an image of the person such as a color image (e.g., a red-green-blue or RGB image) of the person, a depth image of the person, or an image of the person that includes both color and depth information (e.g., a color plus depth or RGB-D image). Such images may be captured by a sensor (e.g., an RGB sensor, a depth sensor, an infrared sensor, etc.), a camera, or another suitable device (e.g., such as a medical imaging device) that is capable of producing a visual representation of the person having a certain pose and body shape. The 2D and/or 3D joint locations may be derived based on 2D and/or 3D features extracted from the image, for example, using one or more convolutional encoders. Examples of convolutional encoders may be found in commonly assigned U.S. patent application Ser. No. 16/863,382, filed Apr. 30, 2020, entitled "Systems and Methods for Human Mesh Recovery," the disclosure of which is hereby incorporated by reference in its entirety.

The joint locations 102 may also be derived from a system or application configured to output the joint location information of a person. Such a system or application may be, for example, another medical imaging system configured to determine and output the joint locations of a person, a human motion capture system that is used in gaming development, animation development, special effects generation (e.g., for motion pictures), etc. Accordingly, the system 100 described herein may be used as an add-on to another system. As such, when referred to herein, providing joint location information to a neural network may include receiving the joint location information from another medical imaging system or human motion capture system and providing the received information to the neural network.

The joint locations 102 may not include all of the joint locations of the person as depicted in an image or output by a human motion capture system. For example, one or more joint locations of the person may be obstructed or unobserved in the image, mis-predicted by an upstream device or program, or otherwise unknown to the system 100. As a result, the joint locations 102 used by the system 100 to predict the pose and shape of a person may only include a subset of the joint locations of the person.

The system 100 may include a pose and shape regressor 104 configured to receive the joint locations 102 (e.g., as an input) and determine a plurality of parameters $\theta$ associated with a pose of the person and a plurality of parameters $\beta$ associated with a shape of the person based on the joint locations 102. The pose and shape regressor 104 may be realized using an artificial neural network (ANN) that comprises a plurality of layers such as one or more input layers, one or more hidden layers, and/or one or more output layers. The input layers of the ANN may be configured to receive the joint locations 102 and pass them to subsequent layers for processing. Each of the input layers may include one or more channels and each channel may be configured to receive data from a respective data source. The hidden layers of the ANN may include one or more convolutional layers, one or more pooling layers, and/or one or more fully-connected (FC) layers (e.g., regression layers). For example, the hidden layers may include a plurality of (e.g., a stack of ten) FC layers with rectified linear unit (ReLU) activation functions and each of the FC layers may include a plurality of units (e.g., neurons) having respective weights that, when applied to features associated with the joint locations 102, regress the pose parameters $\theta$ and the shape parameters $\beta$ based on features associated with the joint locations 102.

In examples, N joints may be represented with a vector: [x1, y1, x2, y2, x3, y3 . . . ], where x and y represent the location of each joint. This may result in a 2N-dimensional vector that corresponds to the x and y of each of the N joints. Responsive to receiving such a vector input, the ANN (e.g., the FC layers of the ANN) may progressively transform the input vector into one of different dimensionality. Each FC unit may be followed by a non-linear activation unit (e.g., an ReLU) and/or the next FC unit. An output vector with K dimensions may be derived based this operation, where K may represent the number of parameters estimated. For example, if the pose parameters $\theta$ have 75 dimensions and the shape parameters $\theta$ have 10 dimensions, then K may be equal to 85 (e.g., K=75+10).

In examples, a joint location may be represented by a feature map such as a binary heatmap, and as such the joint may have a matrix representation. Multiple such matrices (e.g., corresponding to N joints) may be combined to produce an N-channel (e.g., one channel per joint) input to the ANN. The input may be processed through one or more convolutional layers of the ANN before being culminated by the FC units of the ANN to produce a K-dimensional output vector representing the pose parameters $\theta$ and the shape parameters $\beta$.

In examples, the regressed pose parameters $\theta$ may include 72 parameters (e.g., 3 parameters for each of 23 joints and 3 parameters for a root joint) and the regressed shape parameters $\beta$ may include a plurality of coefficients (e.g., the first 10 coefficients) of a principle component analysis (PCA) space. Once the pose and shape parameters are determined, a plurality of vertices (e.g., 6890 vertices based on 72 pose parameters and 10 shape parameters) may be obtained for constructing a human model representing the pose and shape of the person. For instance, the human model may be a statistical parametric differentiable model such as a skinned multi-person linear (SMPL) model that defines a function M ($\beta$, $\theta$; $\Phi$): $\mathbb{R}^{82} \to \mathbb{R}^{3 \times N}$ (where $\Phi$ may represent learned SMPL model parameters) for producing N mesh vertices associated with a 3D mesh of the person. The mesh vertices may be used by a mesh generator 108 of the system 100 to generate a visual representation 110 of the human model, for example, by shaping template body vertices conditioned on θ and β, articulating bones according to the joint rotations indicated by θ (e.g., via forward kinematics), and deforming 3D surfaces with linear blend skinning.

The pose and shape regressor 104 may be configured to recover the pose parameters θ separately or independently from the shape parameters β. Such separation or independence may be accomplished, for example, by applying pose normalization during the recovery operation so that the pose parameters may be estimated without knowledge of the subject's specific body shape and vice versa. The pose parameters θ thus recovered may be body shape independent (e.g., independent of the height and/or weight of the person) and likewise the recovered shape parameters β may be also pose independent (e.g., independent of the joint angles of the person). This way, either of the recovered pose parameters or shape parameters may be used in a system or application (e.g., a human motion capture system) without the other one of the recovered pose parameters or shape parameters.

Figure 2:
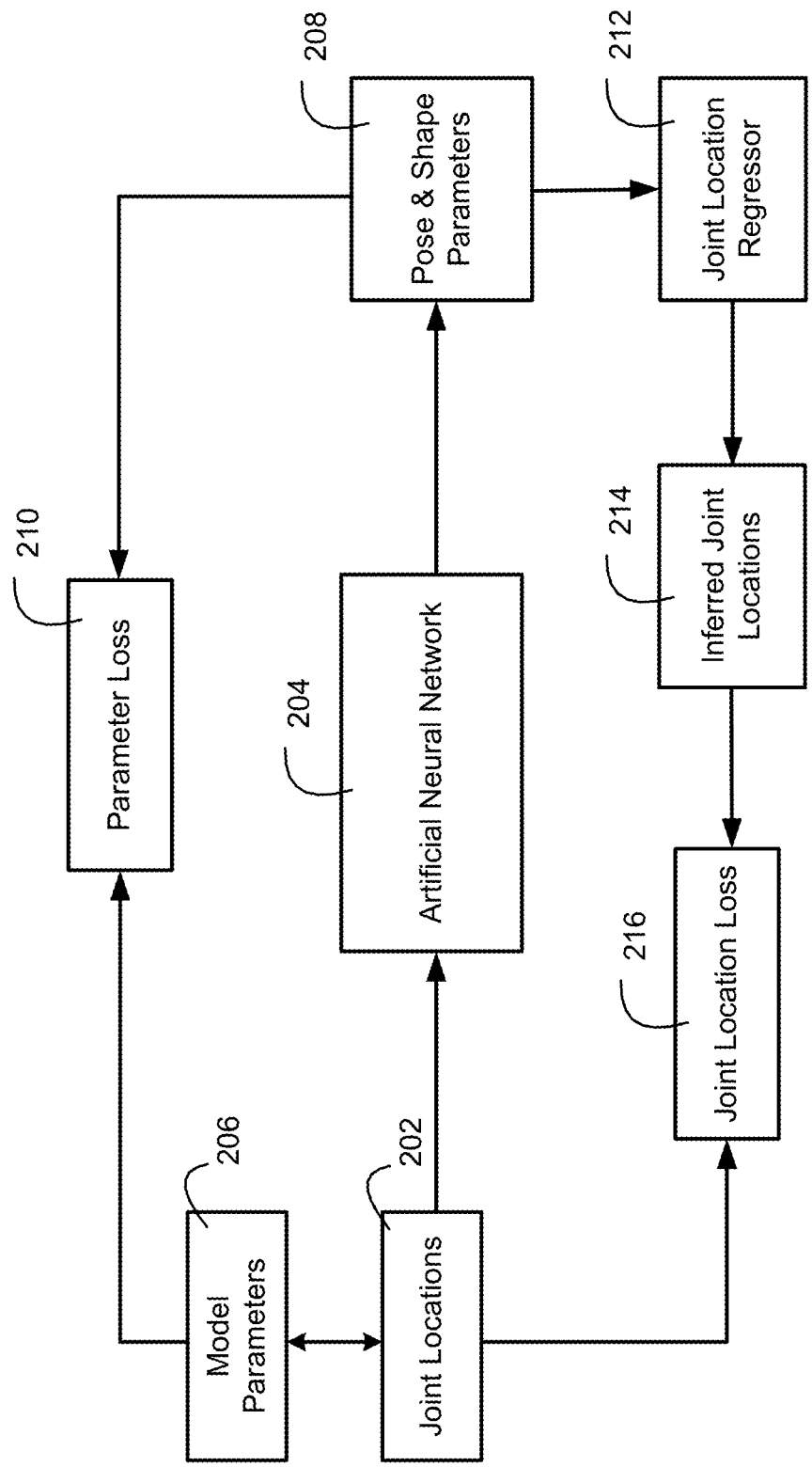
FIG. 2 is a block diagram illustrating an example of training an artificial neural network to learn a model for predicting the pose and shape of a person.

The pose and shape regressor 104 may be trained to predict the pose parameters θ and the shape parameters β using training data that include joint location information of a human body. The joint location information may be paired with human model parameters (e.g., SMPL parameters) to introduce a cycle consistency objective to the training. FIG. 2 is a diagram illustrating an example of training an ANN 204 (e.g., the pose and shape regressor 104) to learn a model for predicting the pose and shape parameters associated with a human model based on joint location information. The training may be conducted using data that include joint location information 202 (e.g., 2D or 3D keypoints or features representing the joint locations) and/or corresponding parameters 206 of a human model from which the joint locations 202 may be derived. Such paired training data may be obtained, for example, from publicly available human motion capture (MoCap) databases and used as ground truth for optimizing the parameters of the ANN 204.

During the training, the ANN 204 may receive the joint location information 202 and predict pose and shape parameters 208 based on the joint location information using initial operating parameters of the ANN 204 (e.g., initial weights associated with one or more fully-connected layers of the ANN 204). The initial operating parameters may be derived, for example, by sampling them from one or more probability distributions and/or based on parameter values of another neural network with a similar architecture. Upon making the prediction, the ANN 204 may compare the predicted pose and shape parameters 208 to the ground truth parameters 206 and calculate a parameter loss 210 in accordance with a loss function. The loss function may be, for example, based on an Euclidean distance between the predicted pose and shape parameters 208 and the ground truth parameters 206, e.g., L'∥[β, θ]−[β̂, θ̂]∥2/2, where [β̂, θ̂] represents the predicted pose and shape parameters 208 and [β, θ] represents the ground truth pose and shape parameters 206. The loss function may also be based on L1 distance, Haussdorf distance, and/or the like.

The ANN 204 may additionally consider a joint location loss when adjusting its operating parameters. For example, the training of the ANN 204 may further utilize a joint location regressor 212 to infer joint locations 214 (e.g., 3D joint locations) based on the predicted pose and shape parameters 208 and adjusting the operating parameters of the ANN 204 by minimizing the difference between the inferred joint locations 214 and the input joint locations 202.

The joint location regressor 212 (e.g., which may comprise a joint regression layer) may be configured to output joint locations based on pose and shape parameters received at an input. The joint locations 214 may be inferred, for example, by applying linear regression to one or more mesh vertices determined from the predicted pose and shape parameters 208 and/or an SMPL model. A joint location loss 216 may be calculated to represent the difference between the inferred joint locations 214 and the input joint locations 202. For example, denoting the input joint locations 202 as J and the pose and shape parameters 208 predicted by the ANN 204 as G(J), the inferred joint locations 214 may be represented by X(G(J)), where X may represent the joint location regressor 212. Consequently, the joint location loss 216 may be calculated in accordance with L"=∥J−X(G(J))∥2/2, and an overall loss function L for training the ANN 204 may be derived as:

$$L=\|[\beta,\theta]-[\hat{\beta},\hat{\theta}]\|2/2+\|J-X(G(J))\|2/2$$

Accordingly, the ANN 204 may adjust its operating parameters (e.g., weights) with an objective of minimizing the overall loss function L. For example, upon obtain the initial pose and shape estimate [β̂, θ̂], the ANN 204 may update its operating parameters via a backpropagation process (e.g., based on a gradient descent of the loss function with respect to the current set of parameters). The ANN may then repeat the prediction and adjustment process described above until one or more training termination criteria are satisfied (e.g., after completing a pre-determined number of training iterations, until the change in the value of the loss function L between consecutive training iterations falls below a predetermined threshold, etc.).

In example implementations, the training of the ANN 204 may be conducted using annotated 2D joint locations (e.g., using only annotated 2D joint locations or using 2D and 3D join locations) as an input. During the training, the ANN 204 may predict the pose and shape parameters 208 based on the input 2D joint locations and infer, via the joint location regressor 212, 3D joint locations based on the predicted pose and shape parameters. To verify the accuracy of the predicted parameters 208, the ANN 204 may project the inferred 3D joint locations onto a 2D image plane to obtain corresponding 2D joint locations (e.g., 2D coordinates, keypoints and/or features indicating the 2D joint locations). The ANN 204 may then compare the projected 2D joint locations with the annotated 2D joint location received at the input and adjust the operating parameters of the ANN 204 based on a loss function associated with the annotated 2D joint locations and the projected 2D joint locations. For example, the projection may be performed based on a weak-perspective camera model and the 2D joint locations may be derived as x=Π(RX (β, θ))+t, where R∈ℝ³ may represent a global rotation in an axis-angle representation, t∈ℝ² and s may correspond to translation and scale, respectively, and Π may denote an orthographic projection. Consequently, the training of the ANN 204 may be conducted with an objective to minimize the loss between the annotated input 2D joint locations and the projected 2D joint locations, which may be represented as L=∥J−x∥2/2 with J denoting the annotated input 2D joint locations. The training may also be supplemented by further considering one or more of a parameter loss (e.g., between input pose and/or shape parameters comprised in the training data and predicted pose and/or shape parameters) or a 3D joint location loss (e.g., between the inferred 3D joint locations and the 3D joint locations comprised in the training data), as described herein.

The ANN 204 may also be trained to predict the pose and shape of a person based on incomplete (e.g., partial) knowledge of the joint locations of the person. As described above, the ANN 204 may only possess such incomplete or partial knowledge of the joint locations of the person because some joint locations of the person may be obstructed, unobserved, or otherwise unknown to the ANN 204. The training of the ANN 204 may account for such situations. For example, during the training of the ANN 204, one or more randomly selected subsets of the joint locations comprised in the training data may be excluded (e.g., marked as unavailable or unobserved) from the input to the ANN 204 and the ANN 204 may be forced to adjust its operating parameters to accommodate the incomplete input (e.g., the ANN may be forced to make prediction that approximates the given ground truth despite having only partial information about the joint locations).

Figure 3:
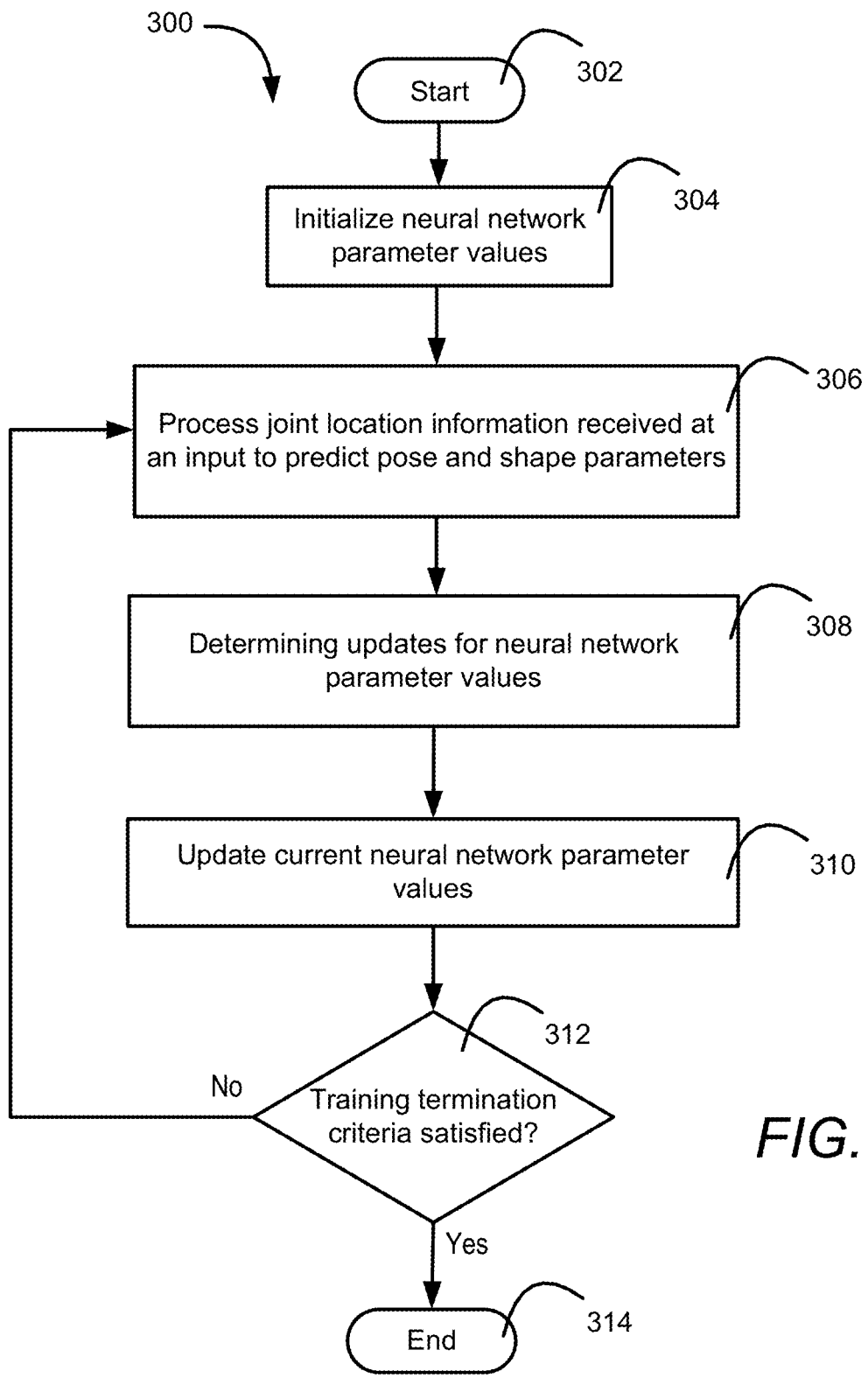
FIG. 3 is a flow diagram illustrating an example neural network training process.

FIG. 3 is a flow diagram of an example process 300 for training a neural network system described herein (e.g., the pose and shape regressor 104 in FIG. 1 or the ANN 204 in FIG. 2). The process 300 may start at 302 and at 304 the neural network system may initialize its operating parameters such as the weights associated with one or more hidden layers (e.g., fully-connected layers) of the neural network system. The parameters may be initialized, for example, by sampling one or more probability distributions or based on parameter values of another neural network with a similar architecture. At 306, the neural network system may receive joint location information associated with a human body at an input and process the joint location information using the initial operating parameters. The neural network system may predict a pose and a shape of the human body based on the input joint location information. At 308, the neural network system may determine the adjustments that need to be made to its operating parameters based on a loss function and a gradient descent (e.g., a stochastic gradient decent) associated with the loss function (e.g., for minimizing the loss function). The loss function may be implemented based on a mean squared error (MSE) or an Euclidean distance between the predicted pose and shape parameters and ground truth parameters (e.g., which may be paired with the joint location information in the training dataset) and/or a MSE or Euclidean distance between the input joint locations and/or joint locations inferred from the predicted pose and shape parameters (e.g., as described herein). The loss function may also take into consideration L1 norm, L2 norm, or L2 norm with L1 norm.

At 310, the neural network system may perform the adjustments to its current operating parameters, for example, via a backpropagation process. At 312, the neural network system may determine whether one or more training termination criteria are satisfied. For example, the system may determine that the training termination criteria are satisfied if the system has completed a pre-determined number of training iterations, if the difference between the predicted parameters and the ground truth parameters is below a predetermined threshold, or if the change in the value of the loss function between two training iterations falls below a predetermined threshold. If the determination at 312 is that the training termination criteria are not satisfied, the system may return to 306. If the determination at 312 is that the training termination criteria are satisfied, the system may end the training process 300 at 314.

The neural network system described herein (e.g., the pose and shape regressor 104 in FIG. 1 or the ANN 204 in FIG. 2) may be implemented using one or more processors, one or more storage devices, and/or other suitable accessory devices such as display devices, communication devices, input/output devices, etc. FIG. 4 is a block diagram illustrating an example neural network system 400 as described herein. As shown, the neural network system 400 may include a processor 402, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The neural network system 400 may further include a communication circuit 404, a memory 406, a mass storage device 408, an input device 410, and/or a communication link 412 (e.g., a communication bus) over which the one or more components shown in FIG. 4 may exchange information. The communication circuit 404 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 406 may include a storage medium configured to store machine-readable instructions that, when executed, cause the processor 402 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 408 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 402. The input device 410 may include a keyboard, a mouse, a voice-controlled input device, a touch sensitive input device (e.g., a touch screen), and/or the like for receiving user inputs to the neural network system 400.

It should be noted that the neural network system 400 may operate as a standalone device or may be connected (e.g., networked or clustered) with other computation devices to perform the functions described herein. And even though only one instance of each component is shown in FIG. 4, a skilled person in the art will understand that the neural network system 400 may include multiple instances of one or more of the components shown in the figure. Furthermore, although the examples are described herein with reference to various types of neural networks, various types of layers, and/or various tasks being performed by certain types of neural networks or layers, those references are made merely for illustration purposes and not meant to limit the scope of the disclosure. In addition, the operation of the example neural network system is depicted and described herein with a specific order. It should be appreciated, however, that these operations may occur in various orders, concurrently, and/or with other operations not presented or described herein. And not all operations that the neural network system is capable of performing are depicted and described herein, and not all illustrated operations are required to be performed by the system.

For simplicity of explanation, the operations of the neural network system may have been depicted and described with a specific order. It should be appreciated, however, that these operations may occur in various orders, concurrently, and/or with other operations not presented or described herein. Furthermore, it should be noted that not all operations that the neural network system is capable of performing are depicted and described herein. It should also be noted that not all illustrated operations may be required to be performed by the neural network system.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A system comprising one or more processors and one or more storage devices storing instructions that, when executed by the one or more processors, cause the one or more processors to:
    implement an artificial neural network;
    provide information regarding one or more joint locations of a person to the artificial neural network, wherein the one or more joint locations correspond to a subset of all joint locations of the person;
    determine, via the artificial neural network, a first plurality of parameters associated with a pose of the person based on the information regarding the one or more joint locations of the person;
    determine, via the artificial neural network, a second plurality of parameters associated with a shape of the person based on the information regarding the one or more joint locations of the person; and
    generate, based on the first and second pluralities of parameters, a human model that represents the pose and shape of the person;
    wherein the artificial neural network is trained to determine the first and second pluralities of parameters and the training of the artificial neural network comprises:
        the artificial neural network receiving training data that comprise a plurality of joint locations of a human body;
        the artificial neural network predicting pose and shape parameters associated with the human body based on the plurality of joint locations comprised in the training data;
        the artificial neural network inferring joint locations of the human body based on the predicted pose and shape parameters; and
        the artificial neural network adjusting one or more of its operating parameters based on a difference between the inferred joint locations and the plurality of joint locations comprised in the training data;
    wherein, during the training of the artificial neural network, a subset of the plurality of joint locations is randomly excluded from an input of the artificial neural network and the artificial neural network is configured to predict the pose and shape parameters associated with the human body without the excluded subset of the plurality of joint locations.

2. The system of claim 1, wherein the training data further comprise pose and shape parameters associated with the plurality of joint locations of the human body and wherein the training of the artificial neural network further comprises the artificial neural network adjusting the one or more of its operating parameters based on a difference between the predicted pose and shape parameters and the pose and shape parameters comprised in the training data.

3. The system of claim 2, wherein the training data are derived from a parametric human model associated with the human body.

4. The system of claim 1, wherein the information regarding the one or more joint locations of the person is derived from an image of the person.

5. The system of claim 4, wherein the image comprises one or more of color information or depth information associated with the one or more joint locations.

6. The system of claim 1, wherein the information regarding the one or more joint locations of the person indicates three-dimensional (3D) joint locations of the person.

7. The system of claim 1, wherein the information regarding the one or more joint locations of the person indicates two-dimensional (2D) joint locations of the person, the training data comprises 2D joint locations of the human body, and the training of the artificial neural network comprises:
    the artificial neural network predicting the pose and shape parameters associated with the human body based on the 2D joint locations comprised in the training data;
    the artificial neural network inferring three-dimensional (3D) joint locations of the human body using the predicted pose and shape parameters;
    the artificial neural network projecting the 3D joint locations into an image space to obtain corresponding 2D joint locations; and
    the artificial neural network adjusting the one or more of its operating parameters based on a difference between the projected 2D joint locations and the 2D joint locations comprised in the training data.

8. The system of claim 7, wherein the information regarding the one or more joint locations of the person indicates 2D and 3D joint locations of the person, the training data comprises 2D and 3D joint locations of the human body, and the training of the artificial neural network comprises:
    the artificial neural network predicting the pose and shape parameters associated with the human body based on the 2D and 3D joint locations comprised in the training data;
    the artificial neural network inferring 3D joint locations of the human body using the predicted pose and shape parameters;
    the artificial neural network projecting the 3D joint locations into the image space to obtain corresponding 2D joint locations; and
    the artificial neural network adjusting the one or more of its operating parameters based on a difference between the projected 2D joint locations and the 2D joint locations comprised in the training data and a difference between the inferred 3D joint locations and the 3D joint locations comprised in the training data.

9. The system of claim 1, wherein the first plurality of parameters associated with the pose of the person is determined independently from the second plurality of parameters associated with the shape of the person.

10. The system of claim 1, wherein causing the one or more processors to provide information regarding the one or more joint locations of the person to the artificial neural network comprises causing the one or more processors to receive the information regarding the one or more joint locations of the person from another system and provide the information to the artificial neural network.

11. A method for predicting pose and shape parameters associated with a person using an artificial neural network, the method comprising:
providing information regarding one or more joint locations of the person to the artificial neural network, wherein the one or more joint locations correspond to a subset of all joint locations of the person;
determining, via the artificial neural network, a first plurality of parameters associated with a pose of the person based on the information regarding the one or more joint locations of the person;
determining, via the artificial neural network, a second plurality of parameters associated with a shape of the person based on the information regarding the one or more joint locations of the person; and
generating, based on the first and second pluralities of parameters, a human model that represents the pose and shape of the person;
wherein the artificial neural network is trained to determine the first and second pluralities of parameters and the training of the artificial neural network comprises:
the artificial neural network receiving training data that comprise a plurality of joint locations of a human body;
the artificial neural network predicting pose and shape parameters associated with the human body based on the plurality of joint locations comprised in the training data;
the artificial neural network inferring joint locations of the human body based on the predicted pose and shape parameters; and
the artificial neural network adjusting one or more of its operating parameters based on a difference between the inferred joint locations and the plurality of joint locations comprised in the training data;
wherein, during the training of the artificial neural network, a subset of the plurality of joint locations is randomly excluded from an input of the artificial neural network and the artificial neural network is configured to predict the pose and shape parameters associated with the human body without the excluded subset of the plurality of joint locations.

12. The method of claim 11, wherein the training data further comprise pose and shape parameters associated with the plurality of joint locations of the human body and wherein the training of the artificial neural network further comprises the artificial neural network adjusting the one or more of its operating parameters based on a difference between the predicted pose and shape parameters and the pose and shape parameters comprised in the training data.

13. The method of claim 11, wherein the information regarding the one or more joint locations of the person is derived from an image of the person.

14. The method of claim 11, wherein the information regarding the one or more joint locations of the person indicates three-dimensional (3D) joint locations of the person.

15. The method of claim 11, wherein the information regarding the one or more joint locations of the person indicates two-dimensional (2D) joint locations of the person, the training data comprises 2D joint locations of the human body, and the training of the artificial neural network comprises:
the artificial neural network predicting the pose and shape parameters associated with the human body based on the 2D joint locations;
the artificial neural network inferring three-dimensional (3D) joint locations of the human body using the predicted pose and shape parameters;
the artificial neural network projecting the 3D joint locations into an image space to obtain corresponding 2D joint locations; and
the artificial neural network adjusting the one or more of its operating parameters based on a difference between the projected 2D joint locations and the 2D joint locations comprised in the training data.

16. The method of claim 15, wherein the information regarding the one or more joint locations of the person indicates 2D and 3D joint locations of the person, the training data comprises 2D and 3D joint locations of the human body, and the training of the artificial neural network comprises:
the artificial neural network predicting the pose and shape parameters associated with the human body based on the 2D and 3D joint locations comprised in the training data;
the artificial neural network inferring 3D joint locations of the human body using the predicted pose and shape parameters;
the artificial neural network projecting the 3D joint locations into the image space to obtain corresponding 2D joint locations; and
the artificial neural network adjusting the one or more of its operating parameters based on a difference between the projected 2D joint locations and the 2D joint locations comprised in the training data and a difference between the inferred 3D joint locations and the 3D joint locations comprised in the training data.

* * * * *